United States Patent
Yeritsyan (10) Patent No.: US 11,324,695 B2
(45) Date of Patent: May 10, 2022

(54) TRANSDERMAL SOLVENT SYSTEM AND METHODS OF USE

(71) Applicant: Donaghys Limited, Christchurch (NZ)

(72) Inventor: Karen Yeritsyan, Dunedin (NZ)

(73) Assignee: Donaghys Limited, Christchurch (NZ)

( * ) Notice: Subject to any disclaimer, the term of this patent is extended or adjusted under 35 U.S.C. 154(b) by 0 days.

(21) Appl. No.: 17/313,994

(22) Filed: May 6, 2021

(65) Prior Publication Data

US 2021/0259966 A1    Aug. 26, 2021

Related U.S. Application Data

(63) Continuation of application No. PCT/NZ2020/050068, filed on Jul. 15, 2020.

(51) Int. Cl.
| | | |
|---|---|---|
| *A61K 9/08* | (2006.01) | |
| *A61K 9/00* | (2006.01) | |
| *A61K 45/00* | (2006.01) | |
| *A61K 47/14* | (2017.01) | |
| *A61K 47/24* | (2006.01) | |
| *A61K 47/44* | (2017.01) | |

(52) U.S. Cl.
CPC .............. *A61K 9/08* (2013.01); *A61K 9/0014* (2013.01); *A61K 45/00* (2013.01); *A61K 47/14* (2013.01); *A61K 47/24* (2013.01); *A61K 47/44* (2013.01)

(58) Field of Classification Search
None
See application file for complete search history.

(56) References Cited

U.S. PATENT DOCUMENTS

| | | | |
|---|---|---|---|
| 4,801,586 | A | 1/1989 | Minaskanian et al. |
| 4,808,414 | A | 2/1989 | Minaskanian et al. |
| 5,759,528 | A | 2/1998 | Fukushima et al. |
| 6,291,401 | B1 | 9/2001 | Dufau et al. |
| 6,759,370 | B1 | 7/2004 | Innes et al. |
| 6,936,572 | B2 | 8/2005 | Brown et al. |
| 8,003,094 | B2 | 8/2011 | Erwin et al. |
| 8,513,311 | B2 | 8/2013 | Acquistapace et al. |
| 8,771,724 | B2 | 7/2014 | Koide et al. |
| 9,006,272 | B2 | 4/2015 | Freehauf et al. |
| 9,040,061 | B2 | 5/2015 | Duan et al. |
| 9,295,626 | B2 | 3/2016 | Grohmann et al. |
| 9,649,299 | B2 | 5/2017 | Yeritsyan |
| RE47,034 | E | 9/2018 | Duan et al. |
| 2008/0153885 | A1 | 6/2008 | Freehauf et al. |
| 2008/0292684 | A1 | 11/2008 | Colombo et al. |
| 2009/0258070 | A1 | 10/2009 | Burnier et al. |
| 2011/0104241 | A1 | 5/2011 | Koide et al. |
| 2011/0195137 | A1* | 8/2011 | Fabries ................ A61K 31/352 424/731 |
| 2012/0041042 | A1 | 2/2012 | Fattohi et al. |
| 2013/0150334 | A1 | 6/2013 | Duan et al. |
| 2013/0274302 | A1 | 10/2013 | Fuchs et al. |
| 2014/0051722 | A1 | 2/2014 | Burnier et al. |
| 2014/0057976 | A1 | 2/2014 | Abbott et al. |
| 2014/0107081 | A1 | 4/2014 | Abbott et al. |
| 2014/0343171 | A1 | 11/2014 | Grohmann et al. |
| 2015/0011596 | A1 | 2/2015 | Fuchs et al. |
| 2015/0283119 | A1 | 10/2015 | Yeritsyan |
| 2016/0008295 | A1 | 1/2016 | Tighe et al. |
| 2016/0008471 | A1 | 1/2016 | Batt et al. |
| 2016/0199343 | A1 | 7/2016 | Alexandre et al. |
| 2016/0271092 | A1 | 9/2016 | Arora et al. |
| 2017/0231231 | A1 | 8/2017 | Enan et al. |
| 2017/0239173 | A1 | 8/2017 | Kajihara et al. |
| 2017/0266289 | A1 | 9/2017 | Lipari et al. |
| 2018/0140610 | A1 | 5/2018 | Nemas et al. |
| 2019/0046438 | A1 | 2/2019 | Hnat |
| 2019/0343796 | A1 | 11/2019 | Noro et al. |
| 2020/0054654 | A1 | 2/2020 | Amarji et al. |

FOREIGN PATENT DOCUMENTS

| | | |
|---|---|---|
| AU | 2012227241 | 4/2013 |
| CN | 103316314 | 9/2013 |
| CN | 108852907 | 11/2018 |
| CN | 109010408 | 12/2018 |
| WO | 2012085160 | 6/2012 |

OTHER PUBLICATIONS

International Search Report and Written Opinion issued in PCT/NZ2020/050068, dated Oct. 16, 2020.

\* cited by examiner

*Primary Examiner* — Nannette Holloman
(74) *Attorney, Agent, or Firm* — ARC IP Law, PC; Joseph J. Mayo (57) ABSTRACT

Described herein are transdermal solvent systems comprising at least one active agent in solution in a base solution, the base solution comprising at least one fatty acid ester compound, at least one monoterpene compound and a co-solvent in the form of DMSO or DMI and at least one plant oil. The base solution was found to be highly versatile and provide superior or at least comparable skin penetration efficacy and active agent compatibility. Methods of treatment, uses of the solvent system and methods of manufacture are also described.

9 Claims, 2 Drawing Sheets

TRANSDERMAL SOLVENT SYSTEM AND METHODS OF USE

RELATED APPLICATIONS

This application claims priority from New Zealand patent application number 755474 dated 16 Jul. 2019, the contents of which are incorporated herein by reference.

TECHNICAL FIELD

Described herein are transdermal solvent systems and methods of use. The transdermal solvent systems comprise at least one active agent in solution in a base solution, the base solution providing skin penetration efficacy and active agent compatibility. Methods of treatment, uses of the solvent system and methods of manufacture are also described.

BACKGROUND ART

Transdermal solvent systems are known in the art and used to deliver many different actives through the skin to animals. This form of agent delivery has a number of advantages over other methods of administration such as oral pathways or injection pathways since administration is generally fast and with minimal contact or interference with the animal. Using the example of farmed animals for context, a transdermal solvent system involves the application of a simple touch to the animal e.g. a sheep, cattle, deer etc on the animal's back and the active then is absorbed through the skin barrier and into the animal blood stream where the active completes in intended function. By comparison, oral delivery or injection involves use of animal securing equipment, more careful or sensitive placement and dosing and, as result, slower processing of animals. Such methods often involve grater animal distress and more labour and time needed to properly treat the animals.

Transdermal administration however has drawbacks too and hence why other modes of administration are still widely used. The key drawbacks may be summarised to issues around formulation and delivery/efficacy.

Without trying to exemplify every possible formulation drawback, selected issues in no particular order may relate to:

- Providing a solvent system that is in solution. Many actives are inherently unstable when in solution and are often sold or stored in bulk as particles or powders. Particles or powders are undesirable in the context of transdermal solvent systems since they are rarely small enough particles to move through the skin barrier. Even when micronized, the particle transfer is less than is the case for a fully solubilised active agent. The challenge is in providing a solvent system that dissolves the active agent or agents and retains stability over time prior to administration;
- Active compatibility. Active agents have many different properties e.g. they may be unstable chemically, they may be hydrophobic, hydrophilic, lipophilic, lyophilic, hydroscopic and so on. An ideal solvent system should ideally address the various active agent properties to stabilise the agent(s) in a solution and even allow for the combining of multiple active agents of differing properties into a single solvent system;
- Solvent system versatility. Some art solvent systems are developed specific to one active agent and when used for another agent, the solvent system no longer is stable or no longer delivers the desired degree of transdermal transport needed for the solvent system to be a viable delivery system. Similarly, some solvent system are developed to only deliver combinations of agents with similar properties e.g. both agents are hydrophobic for example. These narrow range solvent systems, whilst addressing a need are not as versatile as might be desired. A single base solution compatible with many actives agents alone or in combination would be more useful and cost effective than multiple bespoke base solutions;
- Solvent system stability. The time period between solvents system manufacture and administration may be an extended time period i.e. weeks, months or even years. During this time period, the solvent system may be transported, subjected to cold or heat dependent on ambient conditions and subjected to varying humidity's. The length of time and variable storage conditions present a challenge to stability of the solvent system particularly when actives are used that may inherently want to separate or not remain in solution. The solvent system should ideally be stable over time and not separate, reduce active concentration or otherwise deteriorate;
- The solvent system ideally should be low cost to manufacture. Art solvent systems may require costly processing steps during manufacture such as micronizing of particles, use of expensive solvents or use of extensive heating or cooling (energy) during manufacture. These inputs detract from the value of a solvent system since they increase the final product cost and hence commercial success; and
- Viscosity. Solvent systems ideally need to find a compromise in viscosity. A solvent system that is too viscous may be difficult to administer e.g. it may not move rapidly into and out of a dosing gun during administration. High viscosity systems are also harder to dose out correctly. Low viscosity solvent systems on the other hand can also be problematic in that they might run off the animal on administration before sufficient active agent has transferred through the skin barrier.

Further, without trying to exemplify every possible delivery and efficacy drawback, selected issues in no particular order may relate to:

- Skin compatibility. Skin is a living tissue with inherent sensitivity and indeed, the transdermal route of administration is contrary to the primary role of skin i.e. to protect and provide a barrier to the outside world. The solvent system must therefore contravene the primary role of the skin and do so without causing harm. Ideal solvent systems therefore not only deliver active agent through the skin barrier but avoid skin irritation such as rashes, redness, inflammation and other adverse skin reactions;
- Efficacy. Active agent delivery is a key aspect of solvent systems. Insufficient active transfer result in poor commercial success. Of relevance to efficacy is also the depth of penetration of the active agent through the skin barrier and the spread of the agent once through the barrier. An ideal solvent system delivers agent through the barrier to at least therapeutic concentrations and ideally does so as far possible through the skin layer and as widely as possible too so as to encourage subsequent in vivo effects;
- Over-coming wool, hair, grease, dirt and other natural barriers present. Animals rarely present perfectly clean skin surfaces for transdermal treatment. Using farm animals as an example, most animals have hair that the solvent system must work through or around. In the case of woolly animals such as sheep, the wool may prevent direct skin access altogether unless the wool is physically parted. Further to this is the problem of working around other skin covering items like dirt, natural greases, sweat and so on. One option may be to prepare a site using cleaning liquids and trimmers but that is not ideal since these steps take time. Ideally, the solvent system is sufficiently labile and solvating to cut through grease or other direct to the skin site and/or move down hair or wool to the skin layer without needing to perform pre-treatments e.g. the solvent system is simply poured on or spotted on to the animal's back or wool.

As may be appreciated from the above, providing solvent systems that address at least some of the above drawbacks or at least provide the public with a choice may be of benefit particularly given the relative efficiency of administration via the transdermal route versus other administration methods.

Further aspects and advantages of the solvent systems, methods and uses thereof will become apparent from the ensuing description.

SUMMARY

Described herein are transdermal solvent systems comprising at least one active agent in solution in a base solution, the base solution providing skin penetration efficacy and active agent compatibility. Methods of treatment, uses of the solvent system and methods of manufacture are also described. The solvent systems described appear to be highly versatile to be used with almost any active agent, presenting the active agent or agents as a stable solution and with unexpectedly enhanced penetration through the skin barrier. This allows the production of a variety of veterinary medicine and animal care products to be manufactured from a 'stock' or 'base' solution.

For clarity, reference made herein to a solvent solution comprises at least one active agent whilst reference to a base solution refers to the solvent system without active agent present.

In a first aspect, there is provided a solvent system formulated for transdermal administration comprising a therapeutically effective amount of at least one active agent dissolved in a base solution, the base solution comprising:
one or more fatty acid ester compounds;
at least one plant oil having penetration enhancing properties;
at least one emulsifier; and
at least one monoterpene compound.

In a second aspect, there is provided a base solution formulated to carry in solution at least one active agent and to deliver the at least one active agent via transdermal administration, the base solution comprising:
at least one fatty acid ester compound;
at least one monoterpene compound;
dimethylsulfoxide (DMSO) and/or dimethyl isosorbide (DMI);
at least one plant oil;
at least one amphiphilic compound;
at least one compound with emollient and/or humectant properties;
at least one compound that acts is a wetting agent and/or emulsifier; and
at least one diluent compound.

In a third aspect, there is provided a base solution formulated to carry in solution at least one active agent and to deliver the at least one active agent via transdermal administration, the base solution comprising:
10-20% by weight of at least one fatty acid ester compound;
1-14.99% by weight of at least one monoterpene compound;
8-25% by weight dimethylsulfoxide (DMSO) and/or dimethyl isosorbide (DMI);
0.75-5% by weight of at least one plant oil;
0.1-25% by weight of at least one amphiphilic compound;
5-20% by weight at least one compound with emollient and/or humectant properties;
5-10% by weight at least one compound that acts is a wetting agent and/or emulsifier; and
at least one ethylene glycol ether compound as a diluent added to volume q.s.

In a fourth aspect, there is provided a method of treating a non-human mammal, comprising topically administering a solvent system comprising base solution and a therapeutically effective amount of at least one active agent dissolved in the base solution to the non-human mammal in need thereof, the base solution comprising:
one or more fatty acid ester compounds;
at least one plant oil having penetration enhancing properties;
at least one emulsifier; and
at least one monoterpene compound.

In a fifth aspect there is provided a method of:
designing drugs and/or supplements; and/or
treating parasites and/or diseases; and/or
treating nutrient deficiencies,
in a non-human mammal in need thereof by transdermal administration of a solvent system comprising a therapeutically effective amount of at least one active agent dissolved in a base solution, the base solution comprising:
one or more fatty acid ester compounds;
at least one plant oil having penetration enhancing properties;
at least one emulsifier; and
at least one monoterpene compound.

In a sixth aspect, there is provided the use of a solvent system in the manufacture of a medicament for:
designing drugs and/or supplements; and/or
treating parasites and/or diseases; and/or
treating nutrient deficiencies,
to an animal in need thereof,
the solvent system comprising a therapeutically effective amount of at least one active agent dissolved in a base solution, the base solution comprising:
one or more fatty acid ester compounds;
at least one plant oil having penetration enhancing properties;
at least one emulsifier; and
at least one monoterpene compound.

In a seventh aspect, there is provided a method of manufacturing a solvent system comprising a therapeutically effective amount of at least one active agent dissolved in a base solution, the solvent system formulated for transdermal administration, the method comprising the steps:
(a) preparing a base solution comprising:
one or more fatty acid ester compounds;
at least one plant oil having penetration enhancing properties;

at least one emulsifier; and
at least one monoterpene compound;
(b) selecting at least one active agent;
(c) optionally, solubilising the at least one active agent;
(d) adding the at least one active agent to the prepared base solution;
(e) mixing the base solution and at least one active agent until the at least one active agent dissolves into the base solution to form the solvent system; and
(f) optionally, adding one or more preservatives, penetrating agents, diluents, amphiphilic compounds, emollients/humectants and/or wetting agent/emulsifiers.

Selected advantages of the above solvent system include meeting or exceeding design expectations around dissolution and permeation of various active agents via the transdermal route; and avoidance of permanent or long term adverse effects on the animals' skin (and in fact contributes to skin healing after topical application).

The solvent system was found to penetrate animal skin deeper and faster than expected. This rapid rate and depth of penetration may be useful for a variety of reasons such as to prevent any wash off of the solvent system if for example, rain occurs shortly after administration.

The use of plant oils in the solvent system appears to significantly improve penetration of the solvents and active agents present in the solvent system through the animal skin.

Through the use of a specific combination of solvent system components, it is possible to manufacture a solvent system that can not only be used to deliver actives topically with water and/or lipid soluble active ingredients, but also to increase the skin permeability for actives compared to art transdermal products.

Further, one base solution may be used to deliver many different actives and active combinations.

Other advantages are described below in more detail.

DETAILED DESCRIPTION

As noted above, described herein are transdermal solvent systems comprising at least one active agent in solution in a base solution, the base solution providing skin penetration efficacy and active agent compatibility. Methods of treatment, uses of the solvent system and methods of manufacture are also described. The solvent systems described appear to be highly versatile to be used with almost any active agent, presenting the active agent or agents as a stable solution and with unexpectedly enhanced penetration through the skin barrier. This allows the production of a variety of veterinary medicine and animal care products to be manufactured from a 'stock' or 'base' solution.

Definitions

For the purposes of this specification, the term 'about' or 'approximately' and grammatical variations thereof mean a quantity, level, degree, value, number, frequency, percentage, dimension, size, amount, weight or length that varies by as much as 30, 25, 20, 15, 10, 9, 8, 7, 6, 5, 4, 3, 2, or 1% to a reference quantity, level, degree, value, number, frequency, percentage, dimension, size, amount, weight or length.

The term 'substantially' or grammatical variations thereof refers to at least about 50%, for example 75%, 85%, 95% or 98%.

The term 'comprise' and grammatical variations thereof shall have an inclusive meaning—i.e. that it will be taken to mean an inclusion of not only the listed components it directly references, but also other non-specified components or elements.

The term 'treat' or 'treatment' or other grammatical variations thereof in the context of this specification refers to: preventing parasite growth, reduce parasite numbers, killing parasites, killing incoming parasite larvae, lowering the amount of incoming parasite larvae, and/or provide a healing health effect, and/or improve nutrition deficiencies; and combinations thereof.

The term 'solvent system' or grammatical variations thereof refers to a compound or group of compounds in which an active agent or agents are present. For example, selenium compounds may be dissolved in water and added to the solvent system. Therefore, selenium is not dissolved in the actual solvent system, but is present in the solvent system.

The term 'base solution' or grammatical variations thereof refers the solvent system absent of the active agent or agents and any additional solvents that may be used to solubilise the active agent or agents prior to mixing with the base solution. The base solution may be the primary transdermal vehicle for the active agent or agents in the solvent system.

The term 'solution' or grammatical variations thereof as used herein refers to a liquid substantially absent of any solid and/or undissolved particles therein.

The terms 'non-aqueous' and/or 'anhydrous' or grammatical variations thereof refer to the formulation contains one or more solvents and is substantially free of or completely free of water.

The term 'suspension' or 'emulsion' or grammatical variations thereof refers to particles suspended in a liquid solution.

The term 'therapeutically effective amount' or grammatical variations thereof, with reference to an amount or dosage of a composition described herein, refers to an amount of a composition that is sufficient to cause a treatment effect and/or reduction in deficient of a compound in the animal.

The term 'humectant' or grammatical variations thereof refer to a hygroscopic substance that attracts and retains moisture via absorption.

The term 'wettability' or grammatical variations thereof refers to a degree of wetting that is determined by a force balance between adhesive and cohesive forces. Wetting is the ability of liquid to maintain contact with a solid surface, resulting from intermolecular interactions wherein the two are brought together.

Solvent Systems

In a first aspect, there is provided a solvent system formulated for transdermal administration comprising a therapeutically effective amount of at least one active agent dissolved in a base solution, the base solution comprising:
one or more fatty acid ester compounds;
at least one plant oil having penetration enhancing properties;
at least one emulsifier; and
at least one monoterpene compound.

The at least one active agent is fully dissolved in the base solution.

The solvent system is in one embodiment anhydrous.

Base Solutions

In a second aspect, there is provided a base solution formulated to carry in solution, at least one active agent and to deliver the at least one active agent via transdermal administration, the base solution comprising:
at least one fatty acid ester compound;
at least one monoterpene compound;

dimethylsulfoxide (DMSO) and/or dimethyl isosorbide (DMI);
at least one plant oil;
at least one amphiphilic compound;
at least one compound with emollient and/or humectant properties;
at least one compound that acts is a wetting agent and/or emulsifier; and
at least one diluent compound.

In a third aspect, there is provided a base solution formulated to carry in solution, at least one active agent and to deliver the at least one active agent via transdermal administration, the base solution comprising:
10-20% by weight of at least one fatty acid ester compound;
1-14.99% by weight of at least one monoterpene compound;
8-25% by weight dimethylsulfoxide (DMSO) and/or dimethyl isosorbide (DMI);
0.75-5% by weight of at least one plant oil;
0.1-25% by weight of at least one amphiphilic compound;
5-20% by weight at least one compound with emollient and/or humectant properties;
5-10% by weight at least one compound that acts is a wetting agent and/or emulsifier; and
at least one ethylene glycol ether compound as a diluent added to volume q.s.

The base solution is in one embodiment anhydrous.

Active Agent or Agents

The active agent or agents may comprise, but not be seen as limited to compounds with the following functions: nutrient supplements, antibiotics; anti-inflammatories; endo or ecto-parasiticdal compounds, hormonal supplements, antihistamines, antiemetics, metabolic regulators, productivity regulators, hypothyroidism treatments, behavioural treatments, analgesics, insecticides, antibacterials, antifungals, antivirals, antigens, vaccines, a coccidostat, skin-treatment agents, and combinations thereof.

The nutrient supplements may be selected from: water and lipid soluble vitamins, mineral supplements, and combinations thereof. The minerals may be selected from sources of: cobalt, copper, iodine, selenium, zinc, and combinations thereof.

The endo or ecto-parasiticdal compounds may be anthelmintic compounds.

The anti-inflammatory compounds may be non-steroidal or steroidal anti-inflammatory compounds.

The observed compatibility with the base solution also extends to using other active agents than those described above.

Further, the solvent system may comprise multiple active agents for delivery in one dose.

The solvent system may comprise active agents that are soluble in the base solution. In an alternative embodiment, the active agent or agents are solubilised prior to addition to the base solution.

Fatty Acid Esters and Monoterpenes

Fatty acid esters have been identified by the inventor as having a significant role as enhancers, penetrants and moisturisers. In combination with fatty acid esters, monoterpenes were found to add a high degree of stability to the formulation preventing any crystallisation occurring during storage plus no degradation of the activity of the active agents was noted once stabilised as described. Both compounds also confer other useful properties to the base solution, one example being the penetrating activity of the fatty acid esters enhancing the solvent system transdermal properties.

The base solution may in one embodiment comprise approximately: 0.5, or 0.6, or 0.7, or 0.8, or 0.9, or 1.0, or 1.1, or 1.2, or 1.3, or 1.4, or 1.5, or 1.6, or 1.7, or 1.8, or 1.9, or 2.0 or 3, or 4, or 5, or 6, or 7, or 8, or 9, or 10, or 11, or 12, or 13, or 14, or 15, or 15, or 17, or 18, or 19, or 20, or 21, or 22, or 23, or 24, or 25, or 30, or 35, or 45 to 75% by weight of at least one fatty acid compound.

The base solution may comprise approximately 0.5 to 75%, or approximately 1 to 45%, or approximately 1 to 60%, or 2 to 50%, or 5 to 30%, or 10-20% fatty acid ester by weight.

In selected embodiments, the fatty acid ester may be selected from: isopropyl myristate, isopropyl palmitate, octyl dodecyl myristate, ethylhexyl stearate, glyceryl stearate, myristil myristate, stearyl stearate, cholesteryl isostearate, and combinations thereof.

The base solution may comprise approximately: 0.5, or 0.6, or 0.7, or 0.8, or 0.9, or 1.0, or 1.1, or 1.2, or 1.3, or 1.4, or 1.5, or 1.6, or 1.7, or 1.8, or 1.9, or 2.0 or 3, or 4, or 5, or 6, or 7, or 8, or 9, or 10, or 11, or 12, or 13, or 14, or 15% by weight of at least one monoterpene compound.

In one embodiment, the base solution may comprise approximately 1 to 14.99%, or 0.2 to 14%, or 0.5 to 10%, or 0.7 to 5%, or 0.8 to 4% monoterpene compound by weight.

In selected embodiments, the monoterpene may be selected from: camphor, eucalyptol, D-limonene, P-cymem, citranellol, and combinations thereof.

Plant Oil

The term 'plant oil' may refer to a vegetable oil, a herbal oil, a macerated oil or an essential oil and combinations thereof.

As used herein, plant oil refers to oils derived or extracted from plants or parts of plants. The plant parts may be seeds, nuts, kernels, leaves, stems, roots, fruit and so on.

The plant oil may comprise a mixture of oil compounds. The oil compounds may be triglyceride based, the exact composition varying depending on the raw plant material used.

As may be appreciated, the plant oil may also comprise may other compounds besides oil such as vitamins, minerals, tannin compounds, phenolic compounds, plant bioactive compounds, antioxidants, proteins and peptides and so on. Generally, these additional compounds are fat soluble hence why they are extracted with the oil compounds.

In the inventor's experience, this complex mixture of compounds in a natural or organic oil form appears to offer benefit to the solvent system described herein through enhancing permeation of active agents (see more below on this) and minimising any skin harm at the site of administration, perhaps even improving skin condition at the point of administration.

In selected embodiments, the plant oil may be selected from: chamomile oil, frangipani oil, lilac oil, sage oil, seabuckthorn oil, and combinations thereof.

The base solution may comprise approximately: 0.1 or, 0.2 or, 0.3 or, 0.4 or 0.5 or, or 0.6, or 0.7, or 0.8, or 0.9, or 1.0, or 1.1, or 1.2, or 1.3, or 1.4, or 1.5, or 1.6, or 1.7, or 1.8, or 1.9, or 2.0 or 3, or 4, or 5, or 6, or 7, or 8, or 9, or 10, or 11, or 12, or 13, or 14, or 15, or 15, or 17, or 18, or 19, or 20, or 21, or 22, or 23, or 24, or 25, or 30% by weight of at least one plant oil.

The base solution may comprise approximately 0.5 to 10%, or 0.75 to 5%, or 0.1 to 30%, or 0.2 to 25%, or 0.5 to 15%, or 0.75 to 10%, or 0.75-5% plant oil by weight.

It was unexpectedly found that inclusion of plant oil in combination with fatty acid esters and monoterpenes significantly improved penetration of the solvent system through the animal skin. In addition, penetration through animal skin was much deeper compared to commonly used solvents for topical application.

Plant oils are commonly used in topical pharmaceutical formulations as emulsifiers, stabilisers or solubility enhancers. They are presented as safe and inert components, mainly used for formulation purposes. However, the inventor found that plant oil appears to have a penetration enhancing effect on other compounds in the base solution.

Amphiphilic Compounds

In selected embodiments, at least one amphiphilic compound may be used in the base solution.

The amphiphilic compound may have emulsifier properties.

The amphiphilic compound may be water soluble; water absorbing; attract moisture; water dispersible; at least partly hygroscopic; and combinations thereof.

The amphiphilic compound may be a synthetic or natural molecule having the ability to self-assemble into a wide variety of structures including liposomes, bilayer sheets, micelles, vesicles, nanotubes, nanofibers, and lamellae or combinations thereof. The exact structure of self-assembly may be dependent on depending on hydration and temperature.

In one example, the amphiphilic compound may be selected from the group of phosphoglyceride or phosphotide compounds. These are compounds from the group of yellow-brownish fatty substances occurring in animal and plant tissue which are amphiphilic.

The amphiphilic compound may be mixtures of glycerophospholipids including for example: phosphatidylcholine, phosphatidylethanolamine, phosphatidylinositol, phophatidylserine, phosphatidylglycerol and phosphatidic acid.

The phosphoglyceride or phosphotide compounds used in the base solution may comprise for example:
  lecithin;
  hydrogenated lecithin;
  lysolecithin;
  hydrogenated lysolecithin;
  phospholipids;
  hydrolysed phospholipids;
  phosphatidic acid;
  lysophosphatidic acid;
  phosphatidylglycerol;
  lypophosphatidylglycerol;
  phosphatidylserine;
  ammonium phosphatidyl rapeseedate;
  phosphatidylcholine;
  hydrogenated phosphatidylcholine;
  hydrogenated lysophosphatidylcholine;
  lysophosphatidylethanolamine;
  phosphatidylositol.

In one embodiment, the amphiphilic compound may be lecithin. Lecithin was identified by the inventors as a particularly useful base solution compound. Lecithin is a generic term to designate any group of yellow-brownish fatty substances occurring in animal and plant tissues or complex mixture of glycerophospholipids obtained from animal, vegetable or microbial sources, containing varying amounts of substances such as triglycerides, fatty acids, glycolipids, sterols, and sphingophospholipids The lecithin may be natural or synthetic. In naturally occurring lecithin, the phosphoric acid is attached to the glycerol at the α-position. However, the phosphoric acid can also be attached in the β-position of glycerine, as a by-product of synthesis;

The base solution may comprise approximately: 0.1 or, 0.2 or, 0.3 or, 0.4 or 0.5 or, or 0.6, or 0.7, or 0.8, or 0.9, or 1.0, or 1.1, or 1.2, or 1.3, or 1.4, or 1.5, or 1.6, or 1.7, or 1.8, or 1.9, or 2.0 or 3, or 4, or 5, or 6, or 7, or 8, or 9, or 10% or 15% or 25% by weight of at least one amphiphilic compound.

The base solution may comprise approximately 0.1 to 25%, or 0.15 to 20%, or 0.2 to 15%, or 0.25 to 5% amphiphilic substance by weight.

It was unexpectedly found by the inventor that the presence of even small amounts of amphiphilic compounds in the base solution (e.g. lecithin), significantly increased the wetting ability of the base solution and solvent system using the base solution. This feature proved useful in preventing or at least greatly minimising run off of solvent system from an animal when applied topically. This reduction in run off was observed even without an increase in the viscosity of the formulation as would often be the case in art transdermal solutions.

DMSO/DMI Co-Solvent

The base solution may comprise either DMSO or DMI or both compounds. These compounds may act as co-solvents in the base solution and appear to be useful in achieving the desired base solution properties.

In one embodiment, the base solution may comprise approximately: 1.0, or 1.1, or 1.2, or 1.3, or 1.4, or 1.5, or 1.6, or 1.7, or 1.8, or 1.9, or 2.0 or 3, or 4, or 5, or 6, or 7, or 8, or 9, or 10, or 11, or 12, or 13, or 14, or 15, or 15, or 17, or 18, or 19, or 20, or 21, or 22, or 23, or 24, or 25, or 30 or 40, or 50% by weight DMSO, or DMI or a combination of DMSO and DMI.

The base solution may comprise approximately 5 to 45%, or 8 to 25% DMSO, or DMI or both by weight.

The inventor has found that DMSO and/or DMI may assist in the solubilisation and stabilization of some active ingredients in the solvent system and may significantly enhance the miscibility of an active agent or agents into the base solution to form the solvent system.

Excipients

Whilst not essential, the solvent system may further include one or more excipients.

Examples of excipients that may be added comprises: emollients, humectants, diluents, surfactants, antioxidants, and combinations thereof.

Excipients may aid with selected properties of the base solution such as for example, base solution and/or solvent system stability and transdermal effects on administration.

Humectants, emollients, diluents and surfactants are described further below.

The antioxidant is optional. In one embodiment, the antioxidant may be BHT.

Humectant

The humectant if used in the base solution, may be selected based on the humectant also having solvent properties and being physiologically acceptable with animal skin. The humectant may also have emollient properties.

The humectant or humectants may be added to the base solution to volume q.s.

In selected embodiments, the humectant or humectants may be added at a concentration of approximately 5, or 6, or 7, or 8, or 9, 10, or 11, or 12, or 13, or 14, or 15, or 16, or 17, or 18, or 19, or 20% by weight.

In one embodiment 5 to 20%, or 6 to 15%, orb to 12% by weight humectant is present in the base solution.

The choice of humectant or humectant used may be in part governed by their humectant properties but also by their safety for handling as well as compatibility to the animal to which the solvent system is administered. Generally recognised as safe (GRAS) approved humectant may be particularly useful.

In selected embodiments, the at least one humectant may be selected from: propylene glycol, hexylene glycol, butylene glycol, at least one sugar alcohol compound, and combinations thereof.

The sugar alcohol may be selected from: glycerine, sorbitol, xylitol, maltitol, and combinations thereof.

In selected embodiments, the at least one humectant may be a mixture of propylene glycol and either sorbitol or glycerine at a ratio (propylene glycol to sorbitol/glycerine) of approximately 10:1 to 6:1 w/w.

In one embodiment, the humectant may be propylene glycol. In this base solution contact, propylene glycol may have a variety of useful properties beyond just humectant properties including: acting as solvent, acting as a preservative and being GRAS approved.

Surfactant/Wetting Agent

The above base solution may further comprise: 0.25, or 0.5, or 0.75, or 1.0, or 1.25, or 1.5% by weight of at least one surfactant and/or wetting agent.

In one embodiment, the surfactant/wetting agent may be present at a concentration from 0.25 to 15%, or from 5 to 10% by weight.

Examples of surfactant/wetting agents that may be used comprise: polysorbate, EO/PO block copolymers, and combinations thereof. For example, Pluronic PE 6200 or Antarox L64 may be used.

Diluent

The solvent system may further comprise at least one diluent.

The diluent may be added to volume (q.v.) and does not require any specific concentration but for example, may be present at a concentration in the base solution of: 5, or 10, or 15, or 20, or 25, or 30, or 35, or 40, or 45, or 50% w/v. The diluent may be present at a concentration of 5 to 50% w/v, or 15 to 40% w/v.

In one embodiment, the diluent may be selected from one or more ethylene glycol ethyl ether compounds. IN one embodiment, the diluent may be diethylene glycol monoethyl ether (DGME).

Viscosity

The solvent system has a viscosity that remains at a level that is sufficiently low to allow absorption of the active(s) on administration, plus a viscosity that allows use in existing application dosing equipment. Further, the viscosity is not so low that the formulation runs off the application area.

The anticipated viscosity of the formulation is likely to be subject to wide variation as the formulation components may influence viscosity and also, environmental temperatures may also influence viscosity.

In one embodiment, the viscosity may be approximately: 1.0, or 2.5, or 5.0, or 7.5, or 10, or 25, or 50, or 75, or 100, or 150, or 200, or 250, or 300, or 350, or 400, or 450, or 500, or 550, or 600, or 650, or 700, or 750, or 800, or 850, or 900, or 950, or 1000, or 1250, or 1500, or 1750, or 2000, or 2250, or 2500, or 2750, or 3000, or 4000 cP, or 5000 cP.

In one embodiment, the viscosity may range from 1.0 to 2500 cP, or be less than 2000 cP, or be less than 1000 cP, or be less than 500 cP.

Enhanced Penetration/Permeability

It was unexpectedly found that the solvent system enhanced topical penetration/permeability properties formulated for topical application to animals.

A significant advantage of the solvent system is that any active can be dissolved in suitable solvent and following that, dissolved into the solvent system and the solvent system used to improve skin permeability.

For example, selenium may be the active agent and is dissolved in water and then the solution mixed with the base solution described above resulting in a solvent system and, on administration, selenium penetration through cattle skin.

Stability

With respect to stability, the above described solvent systems were tested and found to remain stable for prolonged periods of time in challenging accelerated aging temperatures and humidity's.

The inventor found that the formulation may be stable at accelerated aging conditions of 54° C. and 50% humidity for at least two weeks and at 40° C. and 60% humidity for at least 12 months. Hence, it is envisaged that the solvent system (or base solution) may be stored for an extended period of time without risk of separation or other changes (chemical and/or physical) to the solvent system that might impact on stability or solvent system efficacy.

Methods of Treatment

In a fourth aspect, there is provided a method of treating a non-human mammal, comprising topically administering a solvent system comprising base solution and a therapeutically effective amount of at least one active agent dissolved in the base solution to the non-human mammal in need thereof, the base solution comprising:
    one or more fatty acid ester compounds;
    at least one plant oil having penetration enhancing properties;
    at least one emulsifier; and
    at least one monoterpene compound.

In a fifth aspect there is provided a method of:
    designing drugs and/or supplements; and/or
    treating parasites and/or diseases; and/or
    treating nutrient deficiencies,
    in a non-human mammal in need thereof by transdermal administration of a solvent system comprising a therapeutically effective amount of at least one active agent dissolved in a base solution, the base solution comprising:
    one or more fatty acid ester compounds;
    at least one plant oil having penetration enhancing properties;
    at least one emulsifier; and
    at least one monoterpene compound.

In a sixth aspect, there is provided the use of a solvent system in the manufacture of a medicament for:
    designing drugs and/or supplements; and/or
    treating parasites and/or diseases; and/or
    treating nutrient deficiencies,
    to an animal in need thereof,
    the solvent system comprising a therapeutically effective amount of at least one active agent dissolved in a base solution, the base solution comprising:
    one or more fatty acid ester compounds;
    at least one plant oil having penetration enhancing properties;
    at least one emulsifier; and
    at least one monoterpene compound.

As may be appreciated from the above, the solvent system may be used a number of ways to treat animals. The base solution in particular is in the inventor's experience remarkably versatile with a number of active agent types and the base solution acts as a highly effective vehicle to transfer active agents through the skin barrier without side effects, irritation or running off issues.

Animal

The animal may be a non-human mammal.

In one embodiment, the non-human mammal may be a woolly species of animal. Examples of woolly species of animals may comprise: sheep or lambs, goats, alpaca and llama.

The animal may also be a non-woolly species. The non-woolly species may be selected from the genus: ovine, bovine, porcine and cervine. For example, the animal may be cattle, pigs, deer and companion animals.

Method of Manufacture

In a seventh aspect, there is provided a method of manufacturing a solvent system comprising a therapeutically effective amount of at least one active agent dissolved in a base solution, the solvent system formulated for transdermal administration, the method comprising the steps:

(a) preparing a base solution comprising:
  one or more fatty acid ester compounds;
  at least one plant oil having penetration enhancing properties;
  at least one emulsifier; and
  at least one monoterpene compound;
(b) selecting at least one active agent;
(c) optionally, solubilising the at least one active agent;
(d) adding the at least one active agent to the prepared base solution;
(e) mixing the base solution and at least one active agent until the at least one active agent dissolves into the base solution to form the solvent system; and
(f) optionally, adding one or more preservatives, penetrating agents, diluents, amphiphilic compounds, emollients/humectants and/or wetting agent/emulsifiers.

The inventor has found that the solvent system described herein is simple and inexpensive to manufacture. For example, the lower viscosity and lower shear rates of the base solution and resulting solvent system means easier mixing for less energy input during manufacture. There are no special steps required such has heating, micronizing or vigorous mixing. Having to exert large amounts of energy in order to mix the formulation or on administration is not ideal as, besides added labour or energy costs, mixing may not be as complete as desired.

Storage Container/Applicator

In the above methods and uses, the transdermal formulation may be stored in a tube or plunger for an extended period of time without risk of separation or other changes in the product that might impact on stability.

Further, the formulations may be applied via readily available applicators such as drench guns or other spray systems or simply directly from a syringe or tube. The ability to use existing forms of applicator was unexpected—art formulations often require proprietary administrations devices to be used. In the present case, the inventor found that the formulation efficacy does not depend on application technique, unlike prior art compositions. It was also unexpectedly found that the composition increases skin permeability not only of active ingredients dissolved in it, but also of active ingredients that are dissolved in different solvents, and those of aqueous or non aqueous origin.

Method of Administration

In the above aspects, the method of administration may be by applying the composition to the back of an animal. Administration may be as a stripe or stripes ('pour on'). Administration may be as a spot or spots ('spot on'). A 'stripe' refers to a strip along part or all of the length of the back of an animal. A 'spot' refers to a localised area of application, generally approximately circular in shape. As may be appreciated, one draw back of pour on formulations is that they are generally applied as a stripe or two stripes typically running from the back of neck of animal through to the rump. This requires a moderate volume of formulation and requires uninterrupted application, which is complicated due to the animal moving during application or due to the operator not being used for the full length. Spot on application by the present formulation resolves the above issues related to pour on formulations since only one or more spots need be applied and these need not be in any uniform location.

Advantages

As may be appreciated form the above description, the solvent system, base solution and related methods provide a number of advantages. In no particular order and not intending to be exhaustive, advantages may be as follows:

The solvent system is in solution and presents the active agents in solution. This avoids drawbacks of art particulate suspensions of emulsions and provides a preferred medium for transdermal transfer;

The base solution is compatible with many active agents and active agent combinations avoiding stability issues caused by active agent properties and avoiding active agent deterioration while in the solvent system when stored over time. The ability to provide multiple active agents in one solvent system is useful for a variety of reasons such as minimising dosing operations and frequency and provision of a single base or stock solution useful for many active agents;

The solvent systems described (and base solution) are stable and may be transported, subjected to cold or heat dependent on ambient conditions and subjected to varying humidity's without significant deterioration;

The base solution is relatively low cost to manufacture and does not require any costly processing steps during manufacture such as micronizing of particles, use of expensive solvents or use of extensive heating or cooling (energy) during manufacture;

The solvent system and base solution have a desirable viscosity that avoids run off but is not so viscous as to cause handling issues during dosing, pouring or mixing.

The base solution appears to have no skin irritating effects and in fact appears to actually help heal or moisturise the skin to which it is applied;

Active agent delivery from the base solution vehicle is highly effective based on the inventors work possibly due to transfer through the skin being deeper and/or wider than expected based on knowledge from art transdermal solutions;

The base solution appears to be highly effectively at transferring active agents transdermally even for challenging scenarios where a clear skin patch is not visible or able to be directly administered to. For example, the solvent system described may be applied to the wool of a woolly animal like a sheep and still deliver active agent to the woolly animal. It is understood that the solvent system is mobile enough to run down any hairs or wool and transfer into the animal skin. The solvent system even appears to overcome any barriers from dirt or grease on the animal. This property may be particularly useful since it avoids the need for special pre-treatments such as trimming of hair e.g. the solvent system is simply poured on or spotted on to the animal's back or wool.

The embodiments described above may also be said broadly to consist in the parts, elements and features referred to or indicated in the specification of the application, individually or collectively, and any or all combinations of any two or more said parts, elements or features.

Further, where specific integers are mentioned herein which have known equivalents in the art to which the embodiments relate, such known equivalents are deemed to be incorporated herein as of individually set forth.

BRIEF DESCRIPTION OF THE DRAWINGS

Further aspects of the transdermal solvent systems and methods of use will become apparent from the following Examples that are given by way of example only and with reference to the accompanying drawings in which.

WORKING EXAMPLES

The above described solvent systems, methods of treatment and uses thereof are now described by reference to specific examples.

Example 1

A vitamin B12 containing solvent system is described below in Table 1:

TABLE 1

Example Solvent System

| Function | Compound | Amount (w/v) |
|---|---|---|
| Fatty acid ester | Isopropyl myristate | 10-13% |
| Monoterpene | D-limonene | 1-5% |
| Co-solvent, stabiliser | Dimethyl sulfoxide (DMSO) or dimethyl isosorbide (DMI) | 10-20% |
| Plant oil/penetration enhancer | Seabuckthorn oil | 0.75-5% |
| Amphiphilic compound/Penetration assisting agent | Soya lecithin | 0.1-0.25% |
| Surfactant/wetting agent | Polysorbate 80 | 2.5-7.5% |
| Active agent (vitamin) | Cyanocobalamin (Vit B12) | 0.1-1% |
| Humectant/emollient | Propylene glycol | 5-15% |
| Diluent | Diethylene glycol monoethyl ether (DGME) | To volume q.s. |

Example 2

The solvent system of Example 1 was compared with a commercially available dual anthelmintic pour-on solution to compare active agent transdermal penetration of the Example 1 solvent system (irrespective of active agent) through cattle skin against that of the art product.

Post administration and sufficient time to transfer the active agent(s), tissue biopsies were taken and tested.

This trial was done to test the transdermal properties of the solvent system and how that compared to known art products.

Figure 1:
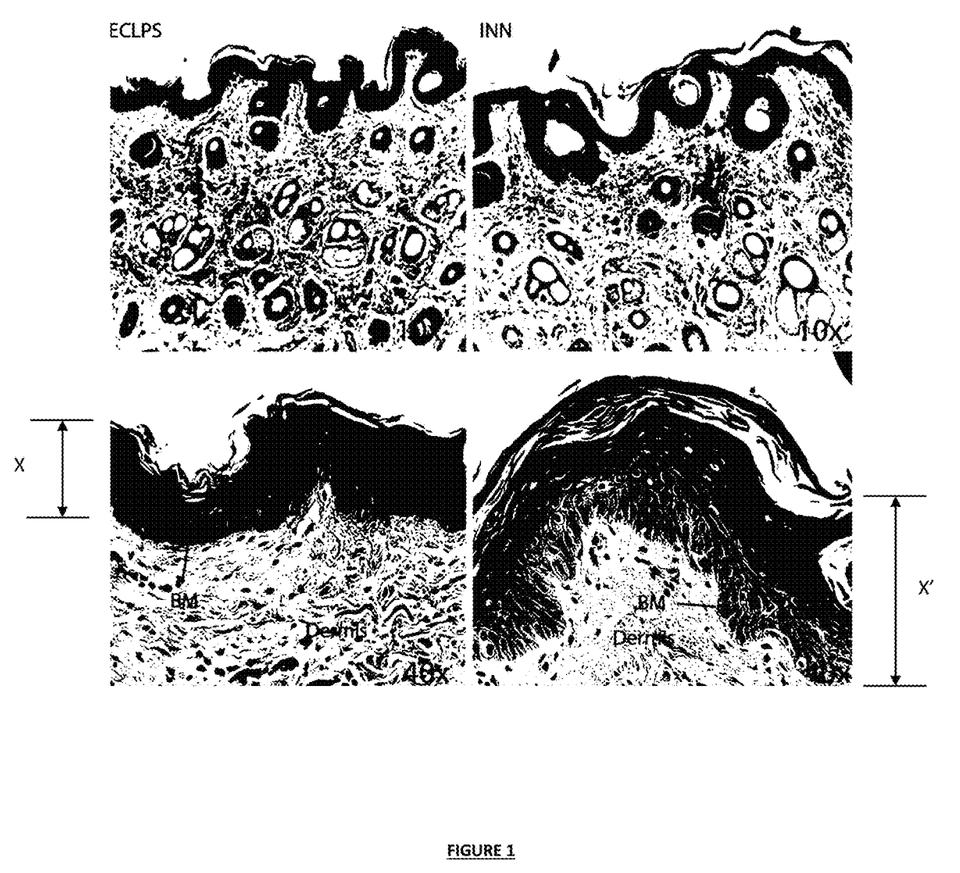
FIG. 1 illustrates Scanning Electron Microscope (SEM) images showing a cross section of cattle skin. The left side images (ECLPS) represent cattle skin penetrated by commercial product, and the right side images (INN) represent cattle skin penetrated by the solvent system of Example 1.

FIG. 1 illustrates four cross-section cattle skin images of the biopsied tissue samples observed using Scanning Electron Microscope (SEM) images. The upper images are SEM images taken at 10× magnification and the lower images are taken at 40× magnification. The left side images (marked ECLPS) represent cattle skin penetrated by the art commercial product, and the right side images (INN) represent cattle skin penetrated by the solvent system of Example 1.

The images show the stratum corneum layer of the epidermis resting on extracellular matrix (ECM) of the dermis underneath. Both compartments are connected by the basement membrane (BM).

As can be seen, particularly in the lower 40× magnified images, the solvent system of Example 1 penetrates through cattle skin significantly deeper (distance X' in FIG. 1) than the art referenced commercial product (distance X in FIG. 1). Further, the solvent system tissue sample shows that the system and agent do not concentrate in the epidermal layer, but spread symmetrically through whole volume of the skin to which it is applied (see the width of the image and common depth of penetration visible through the 40× sample (right and bottom side FIG. 1).

These biopsy results support the inventor's finding that the solvent system enhances transdermal delivery of active agents.

Example 3

The trial completed in Example 2 was further verified in respect of the solvent system of Example 1 transferring the active agent to the animal in vivo by measuring the concentration of vitamin B12 in the animal over time. Samples of blood were taken hourly post administration to look for an increase attributable to the solvent system of Example 1 having been effectively moved across the skin barrier.

Figure 2:
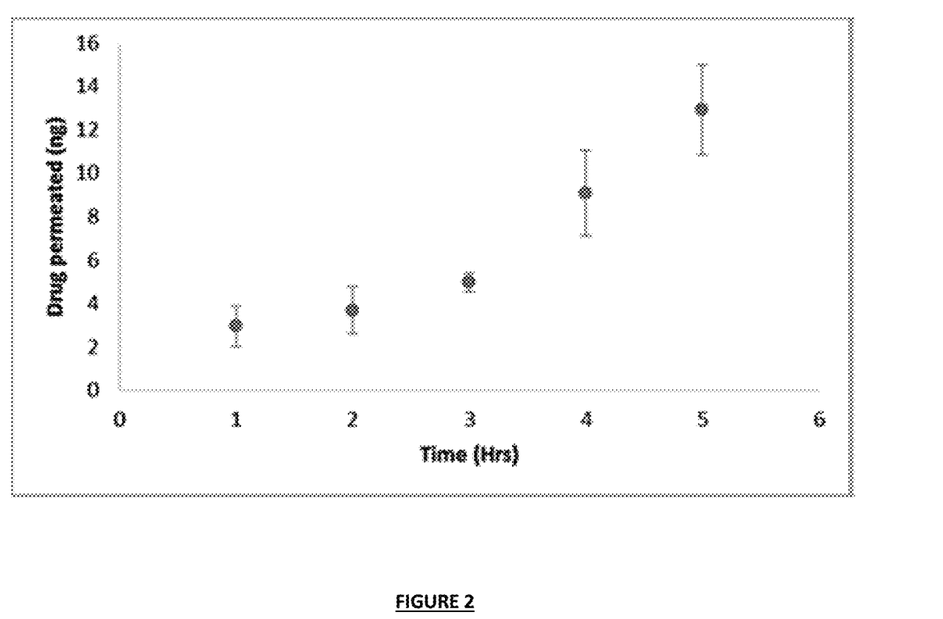
FIG. 2 illustrates a graph of the amount of Vitamin B12 drug permeation (ng) over time when treated with the solvent system of Example 1.

FIG. 2 shows the results where the x axis illustrates the time intervals and the y axis shows the measured level of vitamin B12 permeate (ng). As shown in FIG. 2, the level of vitamin B12 (termed drug permeate in FIG. 2) shows a significant change and increase over time which can only be attributable to the transfer across the skin barrier from the solvent system of Example 1.

As may be appreciated, transfer of vitamin B12 represents a particularly challenging scenario. Vitamin B12 is a relatively large molecule and vitamin B12 has considerable bioavailability within the skin. It might be expected that transfer would be poor to the bloodstream as a result with the skin blocking the larger molecules of vitamin B12 and/or the skin absorbing the B12 and not having it transfer through into the bloodstream. This example clearly shows the benefits of the solvent system in allowing effective transfer even for challenging active agents.

Example 4

A further example of a solvent system is described below in Table 2, this time for transdermal delivery of two compounds with anthelmintic activity having opposing chemical properties i.e. levamisole is water soluble or hydrophilic while eprinomectin is poorly water insoluble and hydrophobic.

TABLE 2

Example Solvent System

| Function | Compound | Amount (w/v) |
|---|---|---|
| Fatty acid ester | Isopropyl myristate | 10-20% |
| Monoterpene | D-limonene | 1-5% |
| Co-solvent, stabiliser | Dimethyl sulfoxide (DMSO) or dimethyl isosorbide (DMI) | 15-25% |
| Plant oil/penetration enhancer | Seabuckthorn oil | 1-3% |
| Amphiphilic compound/ Penetration assisting agent | Soya lecithin | 0.1-0.5% |
| Surfactant/wetting agent | Polysorbate 80 | 2.5-5% |
| Active agent 1 | Eprinomectin | 1-3% |
| Active agent 2 | Levamisole Base | 15-30% |
| Antioxidant | BHT | 0.1-1% |
| Humectant/emollient | Propylene glycol | 5-15% |
| Diluent | Diethylene glycol monoethyl ether (DGME) | To volume q.s. |

Example 5

A further example of a solvent system is described below in Table 3, this time for transdermal delivery of an anti-fungal spray composition for treating ringworms:

TABLE 3

Example Solvent System

| Function | Compound | Amount (w/v) |
|---|---|---|
| Fatty acid ester | Isopropyl myristate | 10-15% |
| Monoterpene | D-limonene | 10-14.99% |
| Co-solvent, stabiliser | Dimethyl sulfoxide (DMSO) or dimethyl isosorbide (DMI) | 8-12% |
| Plant oil/penetration enhancer | Sage oil | 1-2% |
| Amphiphilic compound/ Penetration assisting agent | Soya lecithin | 0.1-0.5% |
| Surfactant/wetting agent | EO/PO block copolymer | 5-10% |
| Active agent | Imidazole | 0.1-0.5% |
| Agent solvent (added to the active agent before mixing with the base solution) | Water | 5-15% |
| Humectant/emollient | Sorbitol | 5-7.5% |
| Diluent | Diethylene glycol monoethyl ether (DGME) | To volume q.s. |

Example 6

A further example of a solvent system is described below in Table 4, this time for transdermal delivery of an anti-inflammatory transdermal formulation:

TABLE 4

Example Solvent System

| Function | Compound | Amount (w/v) |
|---|---|---|
| Fatty acid ester | Isopropyl palmitate | 10-15% |
| Monoterpene | Menthol | 1.5-7.5% |
| Co-solvent, stabiliser | Dimethyl sulfoxide (DMSO) or dimethyl isosorbide (DMI) | 10-20% |
| Plant oil/penetration enhancer | Frangipani oil | 1-5% |
| Amphiphilic compound/ Penetration assisting agent | Soya lecithin | 0.25-0.5% |
| Surfactant/wetting agent | Polysorbate 80 | 5-10% |
| Active agent | Meloxicam | 0.2-0.25% |
| Agent solvent (added to the active agent before mixing with the base solution) | Water | 8-12% |
| Humectant/emollient | Propylene glycol | 10-15% |
| Diluent | Diethylene glycol monobutyl ether (DGME) | To volume q.s. |

Example 7

A further example of a solvent system is described below in Table 5, this time for transdermal delivery of a selenium supplement:

TABLE 5

Example Solvent System

| Function | Compound | Amount (w/v) |
|---|---|---|
| Fatty acid ester | Isopropyl myristate | 15-20% |
| Monoterpene | D-limonene | 4-10% |
| Co-solvent, stabiliser | Dimethyl sulfoxide (DMSO) or dimethyl isosorbide (DMI) | 8-15% |
| Plant oil/penetration enhancer | Lilac oil | 0.75-1.5% |
| Amphiphilic compound/ Penetration assisting agent | Soya lecithin | 0.1-0.5% |
| Surfactant/wetting agent | Polysorbate 80 | 5-10% |
| Active agent | Sodium selenate | 2-5% |
| Agent solvent (added to the active agent before mixing with the base solution) | Water | 10-15% |
| Humectant/emollient | Glycerine | 5-7.5% |
| Diluent | Diethylene glycol monoethyl ether (DGME) | To volume q.s. |

Example 8

A further trial to test the solvent system efficacy was completed. In this example the solvent system described in Example 7 above was administered to a cattle and blood samples then taken hourly post administration and the level of selenium permeate measured.

Figure 3:
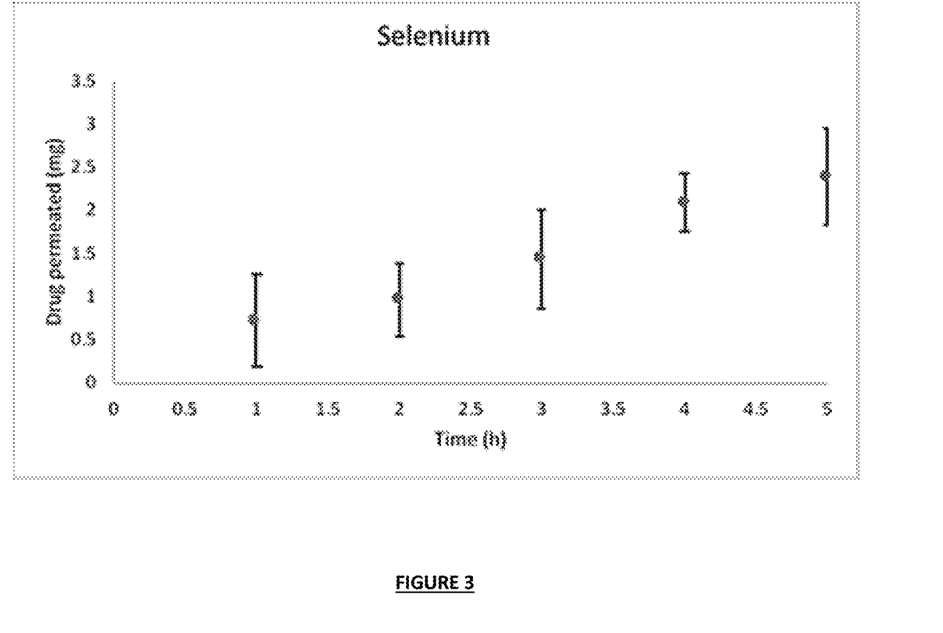
FIG. 3 illustrates a graph of the amount of selenium permeation (mg) over time when treated with the solvent system of Example 5.

FIG. 3 shows the results where the amount of selenium measured as drug permeated (mg) on the y axis of the graph over time increased steadily over time clearly showing transdermal transfer occurred.

Example 9

The efficacy of the solvent system was further tested using the solvent system of Example 4 above.

The solvent system was administered at the calculated dose to the backs of sheep as two separate spots of approximately 20 ml each at the back of the neck and about the rump of the animal (3 groups, n=55 sheep).

The trial was set at a challenging level with no cleaning or special pre-treatment of the wool or skin such as trimming completed prior to administration of the solvent system. The sheep had not been sheared prior to treatment and represented a difficult challenge for transdermal delivery due to the long wool coating (more than 3 inches long), dirt and sebum oil/wax/grease layer on the animal skin, mainly being lanolin.

Measurements of egg were completed from samples taken were taken pre-treatment and on 10 days of post treatment.

Results are shown in Table 6 below of the faecal egg count (FEC) (measured in eggs per gram) before administration and 10 days post administration:

TABLE 6

Faecal Egg Count (FEC) test of dual anthelmintic formulation

| Sheep Groups | Total EPG on day 0 | Total EPG after 10 days post treatment | FEC Reduction % |
|---|---|---|---|
| Group 1 | 112 | 8.5 | 95.9% |
| Group 2 | 259 | 15.11 | 96.8% |
| Group 3 | 175 | 13.6 | 95.8% |
| No Treatment | 476 | 878.9 | 0.0% |

As can be seen from the above table, the results were highly positive with over 95% FEC reduction of the parasite infection from the solvent solution in sheep. These results support the inventors findings that the solvent system provides for excellent transdermal transfer of active agents.

Example 10

The solvent system described in Example 4, Table 2 was subjected to stability testing in accelerated aging storage conditions of 40° C. for 12 months and the results are provided in Table 7 below:

TABLE 7

Tests of stability of dual anthelmintic solvent system

| Active | Initial concentration | Concentration after 6 months | Concentration after 12 months |
|---|---|---|---|
| Eprinomectin | 16.5 g/L | 15.8 g/L | 14.6 g/L |
| Levamisole | 27.15 g/L | 25.45 g/L | 24.1 g/L |

As seen from the above, the concentration of both active ingredients post accelerated aging was less than 15% from the initial formulated concentrations. These results are well within accepted variations and demonstrate active agent stability in the solvent system.

Example 11

The solvent system of Example 4 was tested on sheep directly after shearing (applied directly on the skin) and compared with sheep having wool of 60 mm and over 100 mm long. The trial was completed to test how effective the solvent system is at moving through wool and still achieving the desired efficacy. The results are shown below in Table 8:

TABLE 8

FEC reading on Sheep of Varying Wool Length

| Wool length | FEC Reduction: |
|---|---|
| Off Shear | 99.1% |
| 60 mm | 97.5% |
| Over 100 mm | 99.6% |

As seen from the results above, the presence of wool or not appears to make no difference to the efficacy of the solvent system with the FEC reduction near identical in the trailed animals and irrespective of wool length. These findings support the inventors findings that woolly animals may be treated suing the solvent system with no loss in efficacy and without need to pre-treat the site of administration.

Example 12

To investigate whether there were any adverse effects of the solvent system on the skin of treated animals, a trial was conducted in Roxburgh, Otago (South Island, New Zealand). A base solution (without actives) and the solvent solution of Example 4 (with active) were applied to the skin of sheep using a standard applicator gun.

The animals were observed by a veterinarian daily for any signs of skin irritation, skin redness, swelling at the place of application, along with any wool loss.

It was found that in the case of both the base solution and the solvent system, i.e. without or with actives, there were no significant side effects noticed. Furthermore, any minor effects that were observed had disappeared by day 3 post application.

Example 13

The simplicity of the method of manufacture of the base solution and solvent systems is demonstrated using the solvent system described in Example 1, Table 1.

The method of manufacture involves a simple process of mixing and dissolving. In this example, to manufacture 1000 L of 0.5% vitamin B12 solvent system:
 To a mixing vessel, the following compounds are added in no particular order comprising 130 kg of isopropyl myristate, 10 kg D-limonene, 200 kg of dimethyl sulfoxide or dimethyl isosorbide, 10 kg of seabuckthorn oil, 50 kg of polysorbate 80, 100 kg of propylene glycol, 1 kg of soya lecithin and 100 kg of diethylene glycol monoethyl ether.
 Shortly thereafter, 5 kg of vitamin B12 is added to the solution and the mixture is brought up to volume with the remaining amount of diethylene glycol monoethyl ether.

No intense mixing is required and not heating or cooling is required.

Example 14

The method of manufacture is further demonstrated using the formulation in Example 4, Table 2.

In this example, the following compounds are mixed together in a mixing vessel added in no particular order:
 130 kg of isopropyl myristate, 10 kg D-limonene, 200 kg of Dimethyl sulfoxide, 100 kg of Propylene glycol, 1 kg of Seabuckthorn oil, 1 kg of Lecithin, 100 kg of Diethylene glycol monoethyl ether;
 1 kg of BHT and 27 kg of Levamisole Base; and
 16.5 kg of Eprinomectin;

The above solution is mixed until all the solids are dissolved;

Polysorbate 80 is then added and the solution is brought to volume with diethylene glycol monoethyl ether.

As noted above, the above manufacturing process does not require any specific conditions, such as heating, high shear agitation or any another mixing vessels.

Example 15

A further example of a solvent system is described below in Table 6, this time for transdermal delivery of a dual anthelmintic solution:

TABLE 6

Example Solvent System

| Function | Compound | Amount (w/v) |
| --- | --- | --- |
| Fatty acid ester | Octyl dodecyl nyristate | 10-20% |
| Monoterpene | Camphor | 1-5% |
| Co-solvent, stabiliser | Dimethyl sulfoxide (DMSO) or dimethyl isosorbide (DMI) | 15-25% |
| Plant oil/penetration enhancer | Chamomile oil | 1-3% |
| Amphiphilic compound/ Penetration assisting agent | Hydrogenated lysolecithin | 0.1-0.5% |
| Surfactant/wetting agent | Polysorbate 80 | 2.5-5% |
| Active agent 1 | Eprinomectin | 1-3% |
| Active agent 2 | Levamisole Base | 15-30% |
| Antioxidant | BHT | 0.1-1% |
| Humectant/emollient | Propylene glycol | 5-15% |
| Diluent | Diethylene glycol monoethyl ether (DGME) | To volume q.s. |

Example 16

A further example of a solvent system is described below in Table 7, this time for transdermal delivery of a vitamin B12 solution:

TABLE 7

Example Solvent System

| Function | Compound | Amount (w/v) |
| --- | --- | --- |
| Fatty acid ester | Glyceryl stearate | 15-20% |
| Monoterpene | Pinene | 4-10% |
| Co-solvent, stabiliser | Dimethyl sulfoxide (DMSO) or dimethyl isosorbide (DMI) | 8-15% |
| Plant oil/penetration enhancer | Oregano oil | 0.75-1.5% |
| Amphiphilic compound/ Penetration assisting agent | Soya lecithin | 0.1-0.5% |
| Surfactant/wetting agent | Antarox L64 | 5-10% |
| Active agent | Vit B12 | 2-5% |
| Agent solvent (added to the active agent before mixing with the base solution) | Ethanol | 10-15% |

TABLE 7-continued

Example Solvent System

| Function | Compound | Amount (w/v) |
| --- | --- | --- |
| Humectant/emollient | Sorbitol | 5-7.5% |
| Diluent | Diethylene glycol monoethyl ether (DGME) | To volume q.s. |

Aspects of the solvent systems, methods of treatment and uses thereof have been described by way of example only and it should be appreciated that modifications and additions may be made thereto without departing from the scope of the claims herein.

What is claimed is:

1. A base solution formulated to carry, in solution, at least one active agent and to deliver the at least one active agent via transdermal administration, the base solution comprising:
   10-20% by weight of at least one fatty acid ester compound;
   1-14.99% by weight of at least one monoterpene compound;
   8-25% by weight dimethylsulfoxide (DMSO) and/or dimethyl isosorbide (DMI);
   0.75-5% by weight of at least one plant oil;
   0.1-25% by weight of at least one amphiphilic compound;
   5-20% by weight at least one compound with emollient and/or humectant properties;
   5-10% by weight at least one compound that acts as a wetting agent and/or emulsifier; and
   at least one ethylene glycol ether compound as a diluent added to volume q.s.

2. The base solution as claimed in claim 1, wherein the base solution is anhydrous.

3. The base solution as claimed in claim 1, wherein the at least one plant oil is selected from: chamomile oil, frangipani oil, lilac oil, sage oil, seabuckthorn oil, and combinations thereof.

4. The base solution as claimed in claim 1, wherein the at least one amphiphilic compound is lecithin.

5. The base solution as claimed in claim 1, wherein viscosity of the base solution is less than or equal to 5000 cP.

6. The base solution as claimed in claim 1, wherein the base solution further comprises at least one excipient selected from compounds with: emollient and/or humectant activity, diluents, surfactants/wetting agents, and anti-oxidants.

7. The base solution of claim 1, wherein the at least one active agent is fully dissolved in the base solution.

8. The base solution as claimed in claim 1, wherein the at least one fatty acid ester compound is selected from: isopropyl myristate, isopropyl palmitate, octyl dodecyl myristate, ethylhexyl stearate, glyceryl stearate, myristil myristate, stearyl stearate, cholesteryl isostearate, and combinations thereof.

9. The base solution as claimed in claim 1, wherein the at least one monoterpene compound is selected from: camphor, eucalyptol, D-limonene, P-cymem, citranellol, and combinations thereof.

* * * * *